United States Patent
Sperling (10) Patent No.: US 10,166,058 B2
(45) Date of Patent: Jan. 1, 2019

(54) ACTION/COUNTERACTION SUPERIMPOSED DOUBLE CHAMBER BROAD AREA TISSUE ABLATION DEVICE

(71) Applicant: CORFIGO, INC., Montclair, NJ (US)

(72) Inventor: Jason Sperling, Upper Saddle River, NJ (US)

(73) Assignee: Corfigo, Inc., Montclair, NJ (US)

( * ) Notice: Subject to any disclaimer, the term of this patent is extended or adjusted under 35 U.S.C. 154(b) by 0 days.

(21) Appl. No.: 14/772,654

(22) PCT Filed: Nov. 24, 2014

(86) PCT No.: PCT/US2014/067143
§ 371 (c)(1),
(2) Date: Sep. 3, 2015

(87) PCT Pub. No.: WO2015/081019
PCT Pub. Date: Jun. 4, 2015

(65) Prior Publication Data
US 2016/0338752 A1    Nov. 24, 2016

Related U.S. Application Data

(60) Provisional application No. 61/909,218, filed on Nov. 26, 2013.

(51) Int. Cl.
*A61B 18/02* (2006.01)
*A61B 90/00* (2016.01)
(Continued)

(52) U.S. Cl.
CPC ............ *A61B 18/02* (2013.01); *A61B 90/04* (2016.02); *A61B 18/14* (2013.01); *A61B 18/18* (2013.01);
(Continued)

(58) Field of Classification Search
CPC ............ A61F 2/06; A61B 2018/00023; A61B 2018/00041; A61B 2018/00047; A61B 18/02; A61B 18/025; A61B 18/0256
See application file for complete search history.

(56) References Cited

U.S. PATENT DOCUMENTS

| | | | |
|---|---|---|---|
| 5,846,196 A | 12/1998 | Siekmeyer et al. | |
| 6,858,025 B2 * | 2/2005 | Maurice | A61B 18/02 128/898 |

(Continued)

FOREIGN PATENT DOCUMENTS

| | | |
|---|---|---|
| JP | 2011509711 A | 1/2008 |
| JP | 2013132364 A | 12/2011 |

OTHER PUBLICATIONS

"Stomach." The Columbia Encyclopedia, 6th ed . . . Encyclopedia. com. Nov. 20, 2016 <http://www.encyclopedia.com>.*

(Continued)

*Primary Examiner* — Eun Hwa Kim
(74) *Attorney, Agent, or Firm* — Davis, Brown, Koehn, Shors & Roberts, P.C.; Sean D. Solberg (57) ABSTRACT

A non-linear ablation device includes two opposing surfaces, which are associated with two overlying and separate compartments. A first compartment of the two overlying and separate compartments is configured to emit or resorb energy. A second compartment of the two overlying and separate compartments is configured to either resorb or emit energy to oppose a direction of energy transfer of the first compartment. Other embodiments of the non-linear ablation device are further disclosed.

19 Claims, 6 Drawing Sheets

(51) Int. Cl.
*A61N 7/00* (2006.01)
*A61B 18/14* (2006.01)
*A61B 18/18* (2006.01)
*A61B 18/20* (2006.01)
*A61B 18/00* (2006.01)

(52) U.S. Cl.
CPC ....... *A61B 18/20* (2013.01); *A61B 2018/0016* (2013.01); *A61B 2018/0022* (2013.01); *A61B 2018/00023* (2013.01); *A61B 2018/00041* (2013.01); *A61B 2018/00214* (2013.01); *A61B 2018/00232* (2013.01); *A61B 2018/00791* (2013.01); *A61B 2018/00797* (2013.01); *A61B 2090/049* (2016.02); *A61B 2090/0463* (2016.02); *A61B 2090/0472* (2016.02); *A61B 2090/0481* (2016.02); *A61N 7/00* (2013.01)

(56) References Cited

U.S. PATENT DOCUMENTS

| | | | |
|---|---|---|---|
| 7,179,254 B2 | 2/2007 | Pendekanti et al. | |
| 2003/0125721 A1 | 7/2003 | Yon et al. | |
| 2003/0153905 A1* | 8/2003 | Edwards | A61B 18/1492 606/41 |
| 2004/0006379 A1 | 1/2004 | Brett et al. | |
| 2006/0210605 A1* | 9/2006 | Chang | A61B 17/24 424/434 |
| 2007/0167775 A1 | 7/2007 | Kochavi et al. | |
| 2007/0233226 A1 | 10/2007 | Kochamba et al. | |
| 2007/0287994 A1* | 12/2007 | Patel | A61B 18/1492 606/41 |
| 2008/0077126 A1 | 3/2008 | Rashidi | |
| 2009/0088735 A1* | 4/2009 | Abboud | A61B 18/02 606/22 |
| 2009/0182317 A1* | 7/2009 | Bencini | A61B 18/02 606/21 |
| 2009/0326511 A1* | 12/2009 | Shivkumar | A61B 90/04 604/506 |
| 2011/0034912 A1* | 2/2011 | de Graff | A61B 5/683 606/21 |
| 2011/0282203 A1 | 11/2011 | Tsoref et al. | |
| 2012/0143131 A1* | 6/2012 | Tun | A61B 18/02 604/101.02 |

OTHER PUBLICATIONS

Notification of Transmittal of the International Search Report and the Written Opinion of the International Searching Authority from corresponding PCT/US2014/067143 dated Feb. 19, 2015.

* cited by examiner

ACTION/COUNTERACTION SUPERIMPOSED DOUBLE CHAMBER BROAD AREA TISSUE ABLATION DEVICE

RELATED APPLICATION

This application is a U.S. National Stage Application under 35 U.S.C. § 371 of International Application No. PCT/US2014/067143, filed Nov. 24, 2014, which is hereby incorporated herein by reference in its entirety.

CROSS-REFERENCE TO RELATED APPLICATION

This application claims priority to U.S. Provisional Patent Application No. 61/909,218 filed Nov. 26, 2013, entitled ACTION/COUNTERACTION SUPERIMPOSED DOUBLE CHAMBER BROAD AREA TISSUE ABLATION DEVICE, which is incorporated by reference herein in its entirety.

BACKGROUND OF THE DISCLOSURE

Ablation of living tissue has been used as a therapeutic intervention to cure or improve certain disease states. More specifically, ablation of cardiac tissue has been used to treat a variety of cardiac rhythm disturbances, including those originating in both the atria (upper chambers) and ventricles (lower chambers). Most of these techniques involve the utilization of an energy source (radiofrequency energy, cryothermy, microwave, ultrasound or laser) to destroy living tissue and render such tissue into a scar that is incapable of conducting electrical energy. Regarding atrial fibrillation specifically, most ablative strategies target the pulmonary vein orifices and their transitions to the left atrium, while others are meant to create linear scar lesions within and around the left and right atria themselves. In another technique, balloon cryoablation of the pulmonary vein orifices, creates broad circular lesions by freezing the areas where a balloon is placed to occlude the pulmonary vein, ideally at its junction with the left atrium proper. All of these strategies aim to either encircle or "box-in" target areas, or focally interrupt areas considered to be important sources of atrial fibrillation (always with a major focus on the pulmonary veins).

More recently, the role of the posterior wall of the left atrium heart chamber has been recognized as significant in more "advanced" forms of atrial fibrillation, and its role in "sustaining" atrial fibrillation, possibly by becoming hyper-conductive due to eccentric scar formation. It has been postulated that thorough ablation of both the pulmonary vein origins and the entire posterior wall of the left atrium would be a very effective strategy specifically for advanced forms of atrial fibrillation (including persistent cases), and methods to implement this strategy have been emerging, but the tools are somewhat limited. While pulmonary vein ablation strategies work well in patients with smaller left atrium heart chambers and those who have earlier stage atrial fibrillation (paroxysmal or intermittent), many patients have more persistent forms of atrial fibrillation that cannot be treated successfully with pulmonary vein ablation (or "isolation") alone. There have been attempts to ablate the posterior wall of the left atrium from "within" the left atrium, but in order to be effective, many lesions need to be delivered, each with a small but finite risk of other organ injury, including the airway and the esophagus.

Older surgical strategies (cut-and-sew Maze procedure) have shown reproducible success in these advanced cases, but the surgeries can be risky (require use of the heart-lung machine and cardiac arrest). Attempts to reproduce the extensive surgical lesions using minimally invasive techniques or less invasive tools (compared with "cut and sew") showed some promise, but success rates have been modest and the "minimally invasive" nature has still been considered by most to be substantially invasive.

Among atrial fibrillation experts, it has been widely agreed that anatomically, the pulmonary vein transitions are the source of most of the irregular voltage that typically initiates atrial fibrillation, but in advanced cases, the posterior aspect (back wall) of the left atrium somehow sustains the process of atrial fibrillation, even if the pulmonary veins have been ablated to be electrically isolated from the left atrium. Unfortunately, catheter-based strategies that aim to treat the posterior wall from the inside of the atrium are much more risky procedures than usual because of potential damage to contiguous structures, such as the esophagus, that lie right behind the left atrium that can be injured by inappropriate energy delivery. Further, the results with catheter treatment (called CFAE ablation: complex fractionated atrial electrograms) vary dramatically because the catheter treatment lesions (burns or freezes) are far too small (like point- or spot-welding) to effectively treat (ablate) large and contiguous areas of posterior left atrial tissue. More recently, a linear ablation device has been used that can ablate multiple small strips of the posterior left atrium from the outside (avoiding damage to contiguous organs like the airway and esophagus), but in a piece-meal fashion. The approach has demonstrated good proof of principle for treating persistent forms of atrial fibrillation with a limited experience. The method seems to be more effective than "within-the-left atrium" approaches (catheter ablation), but is tedious to use, as it was intended as a device that creates roughly 3 cm×0.5 cm linear lesions to mimic aspects of the cut-and-sew Maze procedure, but is an imperfect device and method to treat the entire posterior left atrium as it comprises a much larger surface. Another important limitation is that radiofrequency energy algorithms typically self-limit energy delivery with increasing impedance (resistance) of the target tissue, such as occurs with the presence of epicardial fat, which sometimes insulates the posterior left atrial surface and may significantly inhibit ablation. Further, reaching certain parts of the posterior left atrium requires a level of technical proficiency that may be difficult to reproducibly achieve. Since atrial fibrillation is a serious disease that affects one in four Americans over 40 at some point in their lifetime, a treatment that is efficacious/reproducible, less invasive, quick, and easy to learn and apply has dramatic appeal and could save the healthcare system billions of dollars.

SUMMARY OF THE DISCLOSURE

One aspect of the disclosure is directed to a non-linear ablation device comprising two opposing surfaces. The opposing surfaces are associated with two overlying and separate compartments, with a first compartment of the two overlying and separate compartments being configured to emit or resorb energy, and a second compartment of the two overlying and separate compartments being configured to either resorb or emit energy to oppose a direction of energy transfer of the first compartment.

Embodiments of the device may be configured so that the first compartment resorbs energy by cryothermy or freezing (e.g., shuttling and venting gas, such as nitrogen oxide (N₂O) or Argon, or another suitable gas) and the second compartment emits energy or insulates against croythermy (for example, by either active warming with an energy source or by circulating and venting tepid or warm saline or other fluid) to prevent energy resorption below the first compartment, where energy resorption (ablation by freezing) would not be intended.

The first compartment may emit energy by radiofrequency, ultrasound, microwave, magnetism or laser. The second compartment may then utilize a cooling mechanism, which could be accomplished with gas shuttling, such as N₂O or Argon, or with continuous infusion of tepid or cool saline (or other) solution that is vented outside the chamber after circulation and absorption of excess energy.

At least one port may communicate with each of the two compartments individually. The at least one port may be used for shuttling gas or liquid, or to power/control electrical components, such as radiofrequency, laser or ultrasound.

The surface of at least one compartment may be generally shaped like a quadrilateral with one corner displaced further away from the other three corners (usually the lower left corner as shown and described herein) compared with how the other three corners are located with respect to one another.

The compartments may be expandable from a smaller collapsed shape. The device may be collapsible or expandable by a roll-up mechanism; the device can be unrolled or expanded by infusing gas or liquid into the compartments or by another mechanical method. At least one of the compartments may have integrated temperature sensors. Surfaces of at least one of the compartments may be generally convex. Each surface may have a surface area of at least six cm².

Another aspect of the disclosure is directed to a method for ablating a broad and generally large planar area of tissue while heating or cooling a surface opposite an ablation target area to prevent ablation of an opposite surface.

Embodiments of the method may be achieved by a non-linear ablation device having two opposing surfaces. The opposing surfaces may be associated with two overlying and separate compartments, with a first compartment of the two overlying and separate compartments being configured to emit or resorb energy, and a second compartment of the two overlying and separate compartments being configured to either resorb or emit energy to oppose a direction of energy transfer of the first compartment. Each surface may have a surface area of at least six cm². The first compartment may resorb energy by cryothermy or freezing and the second compartment may emit energy or insulate against croythermy.

Yet another aspect of the disclosure is directed to a non-linear ablation device comprising two opposing surfaces. Each surface has a surface area of at least six cm². The opposing surfaces are associated with two overlying and separate compartments, with a first compartment of the two overlying and separate compartments being configured to emit or resorb energy, and a second compartment of the two overlying and separate compartments being configured to either resorb or emit energy to oppose a direction of energy transfer of the first compartment. The non-linear ablation device is expandable from a smaller initial, collapsed configuration.

Another aspect of the disclosure is directed to a non-linear ablation device comprising two opposing surfaces. Each surface has a surface area of at least six cm². The opposing surfaces are associated with two overlying and separate compartments, with a first compartment of the two overlying and separate compartments being configured to resorb energy by cryothermy or freezing, and a second compartment of the two underlying and separate compartment being configured to emit energy to oppose the cryothermy of the first compartment.

A further aspect of the disclosure is directed to a non-linear ablation device comprising two opposing surfaces. Each surface has a surface area of at least six cm². The opposing surfaces are associated with two overlying and separate compartments, with a first compartment of the overlying and separate compartments being configured to emit or resorb energy, and a second compartment of the two underlying and separate compartment being configured to either resorb or emit energy to oppose a direction of energy transfer of the first compartment. The surface of the device is shaped like a quadrilateral with one corner displaced/elongated further away from the other three corners compared with the other three corners, which are located with respect to one another. The displace/elongated corner may be the left lower corner, as shown and described herein.

Another aspect of the disclosure is directed to a device having a surface area with a drooping/elongated lower left corner, the surface area may comprise a more stepwise elongation towards the left lower corner of the device as shown and described herein. This arrangement enables more rigid sub-components to be incorporated into the ablation compartment of the device, such as microwave or ultrasound cells or radiofrequency/energy coils of differing lengths.

A further aspect of the disclosure is directed to a non-linear ablation device comprising two opposing surfaces, each surface having a surface area of at least six cm². The opposing surfaces are associated with two overlying and separate compartments, with a first compartment of the two overlying and separate compartments being configured to resorb energy by cryothermy or freezing, and a second compartment of the two underlying and separate compartments being configured to emit energy to oppose the cryothermy of the first compartment. The non-linear device is expandable from a smaller initial, collapsed configuration. The surface of at least one compartment is generally shaped like a quadrilateral with one corner displaced further away from the other three corners.

The device described overcomes technical limitations of current approaches of posterior left atrium surface ablation by ablating a large and appropriate sized area of the posterior left atrium that can overcome limitations of radiofrequency energy ablation, while protecting adjacent (unintended) areas from ablation injury by providing a size-matched simultaneous counter-action to the ablative energy source. An important iteration is a device that is deployed from a smaller size, so as to be used for a minimally invasive procedure. Other aspects of the disclosure that facilitate easier implementation are surface shapes that generally match those of the posterior left atrium, which has an eccentric shape that is like a rectangle with a drooping/extending left lower corner.

BRIEF DESCRIPTION OF THE DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings.

DETAILED DESCRIPTION

A device for simultaneous ablation of a relatively large surface area of tissue whose shape can be in contact with much or all of the available surface area of the posterior (back) wall of the left atrium is disclosed herein. The device can be polar, having a front surface and a back surface, with only one surface intended to be in contact with the posterior left atrium, and the other surface being opposite the posterior left atrium. Generally, the device shape can be non-linear, and the front surface and the back surface can be flat or convex and exceed six cm$^2$ in surface area. The shape of the posterior left atrium can be complex and eccentric, but generally can be considered to be similar to a quadrilateral with non-parallel sides and rounded edges, with a tapering and increasing inferior aspect moving from right to left.

In one embodiment, a device that can thoroughly ablate the entire left atrium in ideally one ablation, or, for example, in less than four ablations, is shown and described. In addition, the device can be ideally deployed using established minimally invasive approaches to the posterior left atrium, and in these cases would be expandable from a smaller collapsed initial configuration. An energy source ideally can be one that overcomes epicardial fat-insulation limitations of radiofrequency ablation algorithms so that all of the posterior left atrium can be successfully and quickly ablated with minimal risk. Adjunctive procedures, such as cryoballoon ablation of the pulmonary veins, are added to complete the ablation procedure.

In a major iteration, the device is expandable from a collapsed configuration into a relatively flat or convex bladder (compartment) or overlying set of bladders (compartments) that is/are delivered into the posterior pericardium (beneath the posterior left atrium) using video surgery or through a direct approach below the heart, and ablating a broad surface area of the posterior left atrium while protecting against underlying adjacent organ injury. While the energy source described herein is cryothermy, it is conceivable that alternate energy sources could be used as well, such as radiofrequency, microwave, magnetism, ultrasound or laser. An important feature of the device is counteraction of the posterior left atrial cooling or heating either by insulation or with broad-area provision of opposing warming or cooling action in an opposing bladder (compartment) to protect adjacent tissues opposite to the posterior (back) wall of the left atrium. The ablation surface or chamber may separate from an anti-ablation chamber by a septum, or, there may be two independent but superimposed chambers or bladders.

In one embodiment, the device is delivered into position as a collapsed item that is expandable or inflatable by being filled with gas or liquid or by any other mechanism. When expanded, the device can achieve a square, rectangular, oval, circular, and trapezoidal or another shape. A preferred iteration is a single device that is designed in the general shape of the posterior surface of the human left atrium, having a generally quadrilateral or rectangular shaped device with four corners or poles, and with one corner that is elongated and/or widened, with the surface area of the device generally being over six cm$^2$ in area. In one embodiment, the device is shaped like a quadrilateral with the left lower corner displaced further away from the other three corners compared with how the other three corners are located with respect to one another. The ablation surface or chamber, which will ultimately be placed in contact with the back wall of the left atrium, is activated, loaded or charged with an ablation capacity, as by freezing or heating, and the anti-ablation chamber (on the polar opposite side of the ablation chamber/surface, and generally of similar dimensions) is loaded or charged with a warming or cooling capacity or some other method of protecting structures adjacent from the posterior left atrium from injury.

The device may include two plastic (e.g., polyurethane) compartments or bladders, the ablation chamber being infused with a liquid or gas, such as nitric or nitrous oxide, argon or helium, to achieve sub-zero temperatures, while the anti-ablation chamber is infused with warmed gas or liquid solution, or by any means to emit heat or energy. The anti-ablation portion can be a protective or insulating barrier and not require shuttling of gas or liquid. One or both chambers may contain integrated thermometers to monitor dynamic and steady-state temperatures during the ablation process in order to achieve and maintain specified targets for completeness of ablation as well as protection from injury. The device could generally work like a double-sided bladder that is placed behind the left atrium heart chamber. One side of the bladder may be positioned in direct contact with the posterior (back) wall of the left atrium, while the other side of the device/bladder may be in contact with the posterior pericardial sac, but not with the left atrium or heart itself. The anti-ablation part of the device protects structures on the other side of the pericardial sac in that area (esophagus, aorta, lung, airway, nerves, and diaphragm, for example). After the ablation sequence is completed, an expandable device can then again be partially or completely collapsed again for retrieval.

Figure 1A:
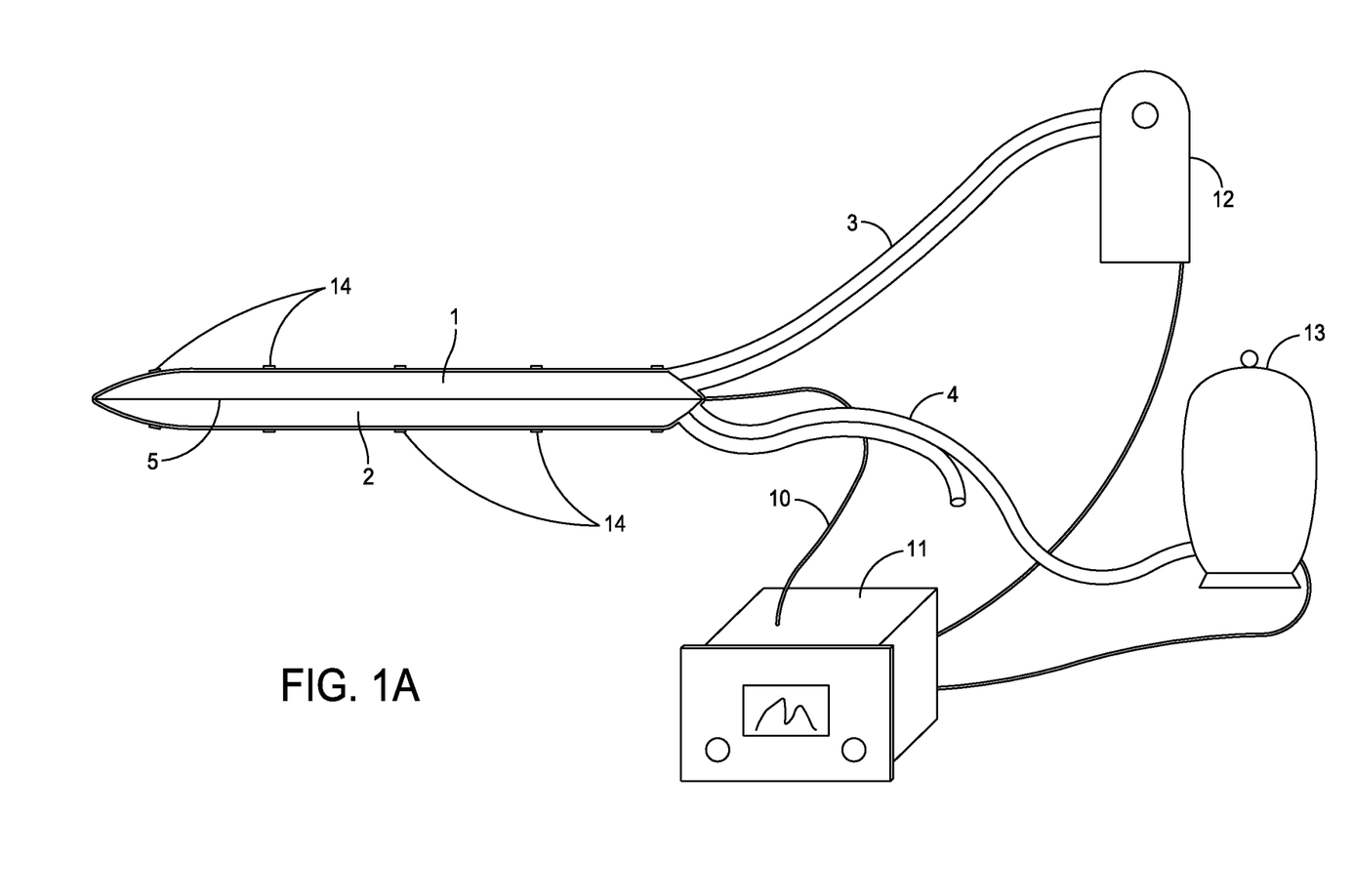
FIG. 1A shows a device in an deflated condition from its right side, the device including an upper ablation chamber that is superimposed over a lower (anti-ablation) chamber that may or may not be expandable.
Figure 1B:
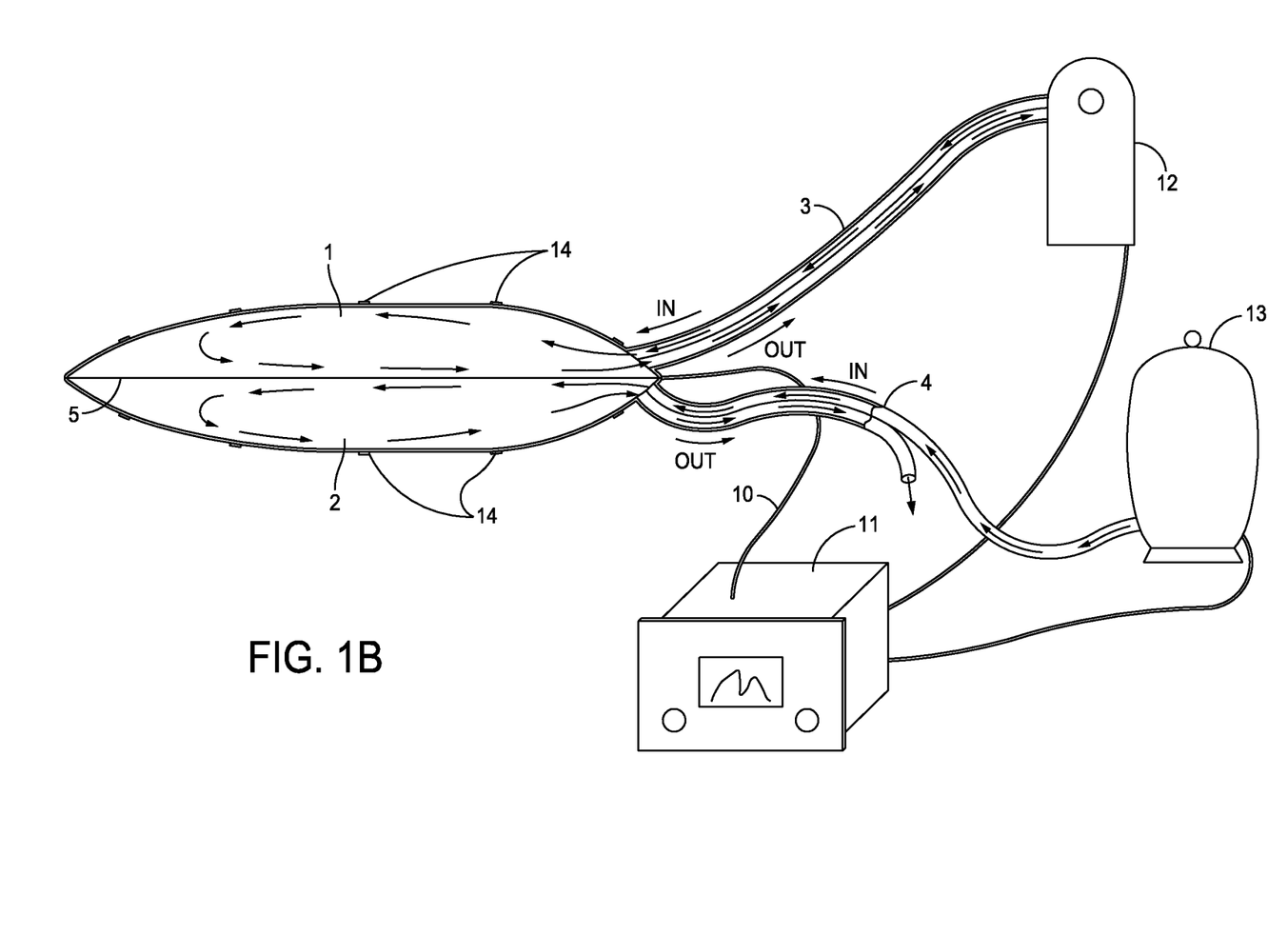
FIG. 1B shows the device in an inflated condition.

Referring to the drawings, FIG. 1A illustrates a device in a deflated condition having a body with two superimposed compartments 1, 2. Each compartment 1, 2 has a generally flat or convex surface area that may or may not be expandable. In a certain embodiment, the device is connected to an electrical line 10 connected to a controller 11 for controlling the operation of energy sources or for filling or releasing the compartments 1, 2 with gas or liquid by ports 3, 4, among other things. Ports 3 or 4 may be complex electrical controllers that actuate a microwave, ultrasound, laser or other mechanism that is embedded within a compartment that causes heating or cooling. FIG. 1B illustrates the same device having an expanded ablation compartment 1 and an expanded anti-ablation compartment 2. The surface areas are convex in this shown embodiment. The controller 11 can supply power to electrical energy sources or fluid or gas sources that are provided to the compartments 1, 2 by ports 3 and 4, which are dedicated to the ablation compartment and to the anti-ablation compartment, respectively. In one embodiment, there may be a shared septum 5 that separates ablation compartment 1 from anti-ablation compartment 2. The septum 5 is configured to have insulating properties.

Figure 2:
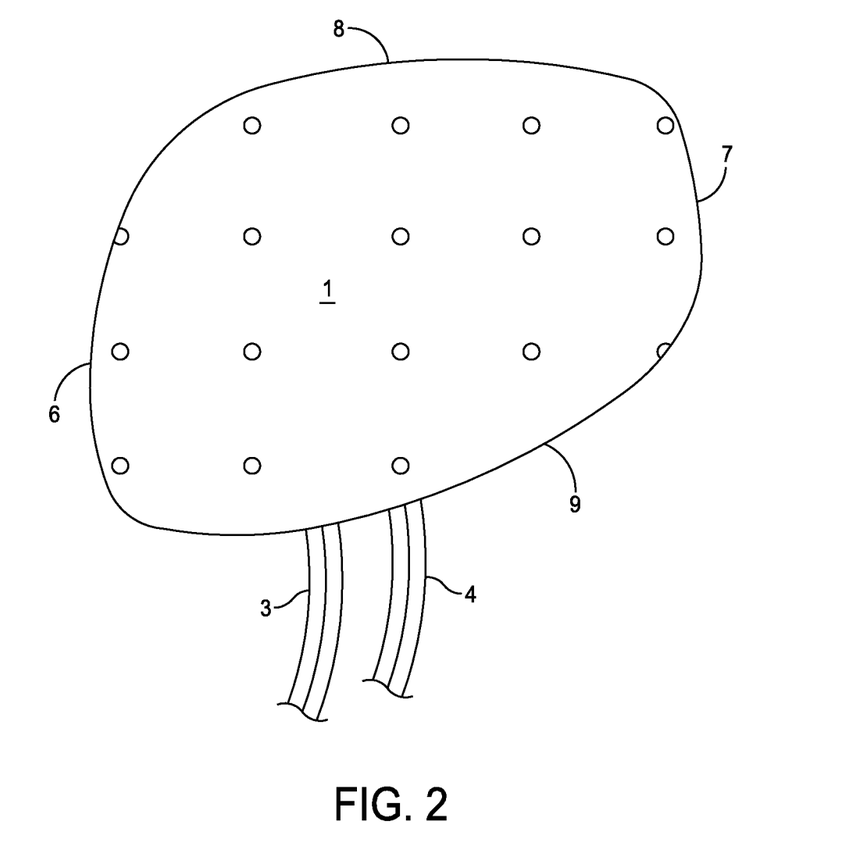
FIG. 2 shows a top view of a device shaped like a posterior left atrium, with a quadrilateral having smooth transitions in the corners, and a lower left corner being displaced away from the others.

Referring to FIG. 2, the device is in the shape of a quadrilateral with smooth transitions in the corners, with the lower left corner being displaced away from the others, looking down upon ablation compartment 1. As shown, port 3 delivers and recycles gas or liquid in (or provides power to) chamber 1, while port 4 uniquely accesses anti-ablation compartment 2, which is positioned behind compartment 1. The shape of this device conforms to the general shape of the posterior wall of the left atrium, with margin 8 being superior (dome of the left atrium), margin 7 abutting the left-sided pulmonary veins posteriorly, margin 6 abutting the right sided pulmonary veins posteriorly, and margin 9 abutting the most inferior aspect of the posterior left atrium, near its junction with the anatomic structure known as the coronary sinus. It should be noted that the left lower corner is displaced away from the rest of the quadrilateral.

Figure 3A:
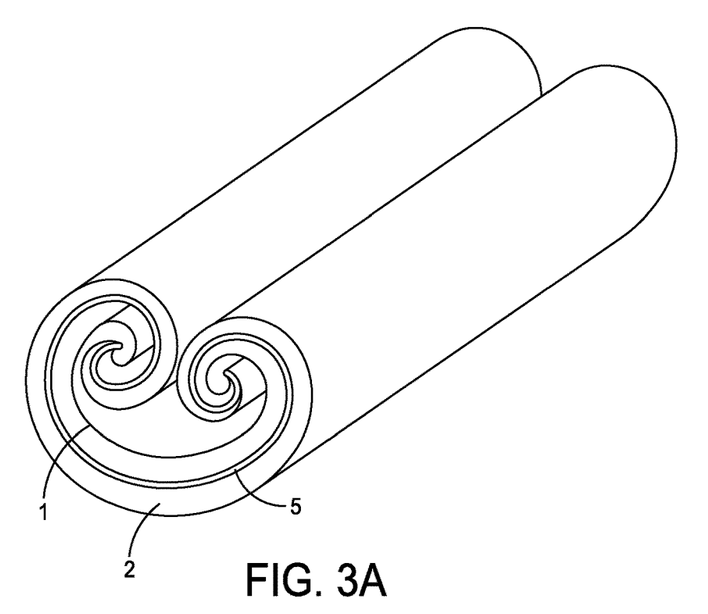
FIGS. 3A-3C show a collapsed device that is rolled up from the left and right sides, transitioning to an opened configuration of the device.
Figure 3B:
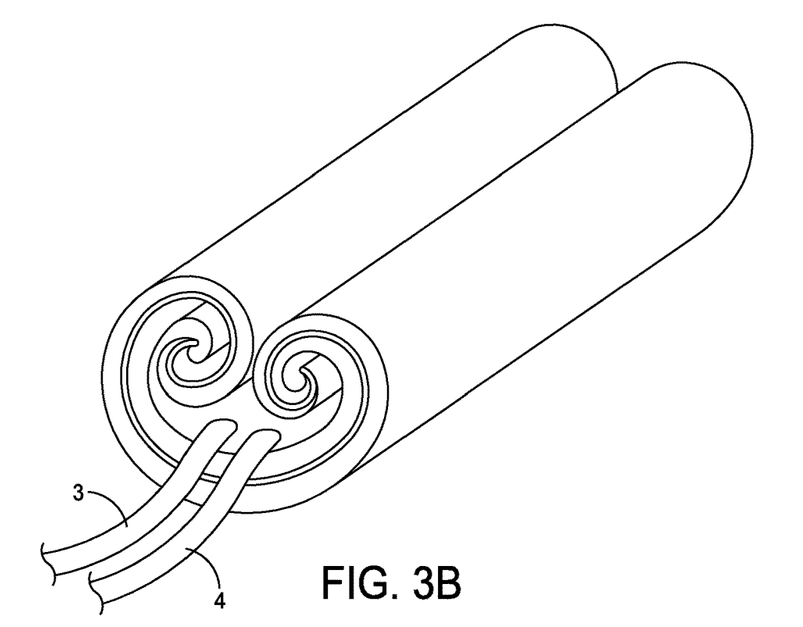
Figure 3C:
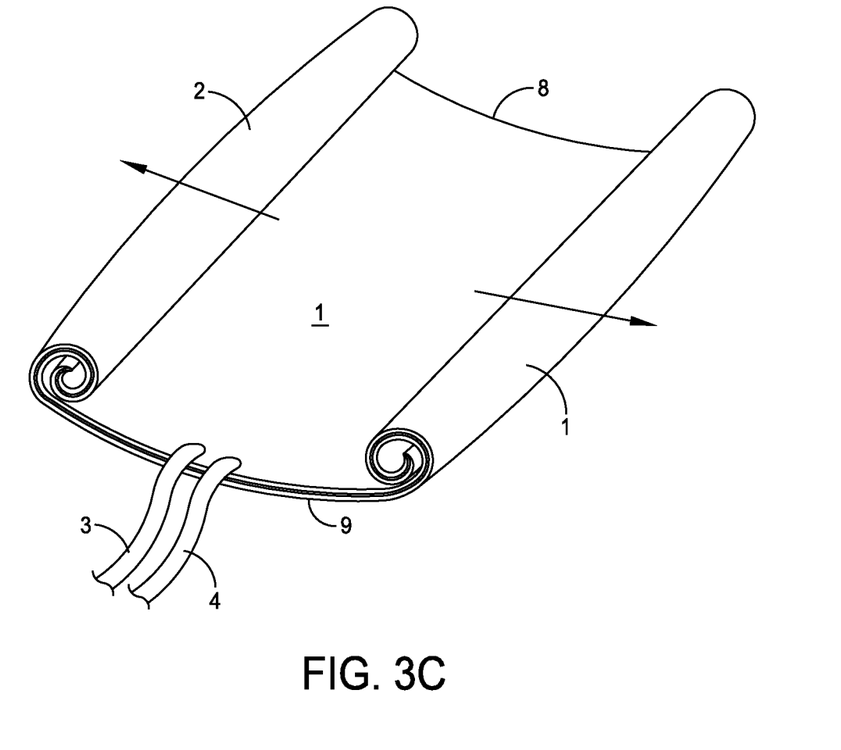

Referring to FIGS. 3A-3C, FIGS. 3A and 3B show the body of the device in a collapsed configuration, rolled up onto itself from both the left and right sides. In this example, the specific pattern of rolling allows for the anti-ablation compartment 2 to be on the bottom or external aspect of the rolled up device, while the ablation compartment 1 is on the internal aspect. FIG. 3B shows a more complete view of the device, with ports 3 and 4 connected to the rolled up device at its trailing end, e.g., by margin 9 shown to be deployed in FIG. 2. FIG. 3C shows the device partially expanding or unfurling, with the anti-ablation compartment 2 being rolled out underneath of ablation compartment 1, which is being exposed by the device unfurling. The leading end of the device, e.g., margin 8, is advanced underneath the heart (not shown), where once unfurled, the ablation compartment 1 comes into direct contact with the posterior wall of the left atrium.

Figure 4A:
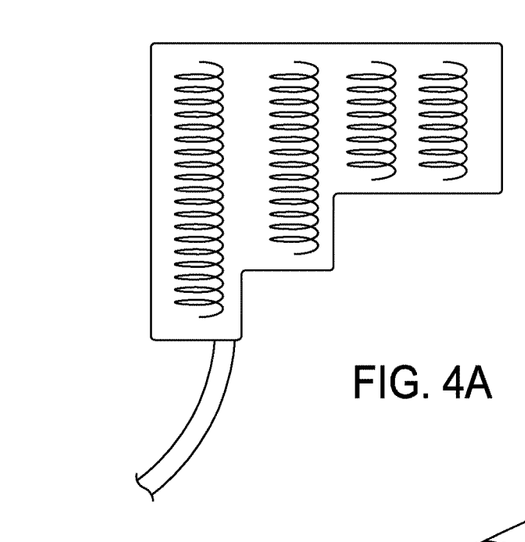
FIG. 4A-4C show a device with a stepwise increase in surface area moving from right to left, with increases occurring towards the left lower corner or pole of the device when viewed in plan, with the device iterations utilizing microwave or ultrasound cells or differing length radiofrequency coils.
Figure 4B:
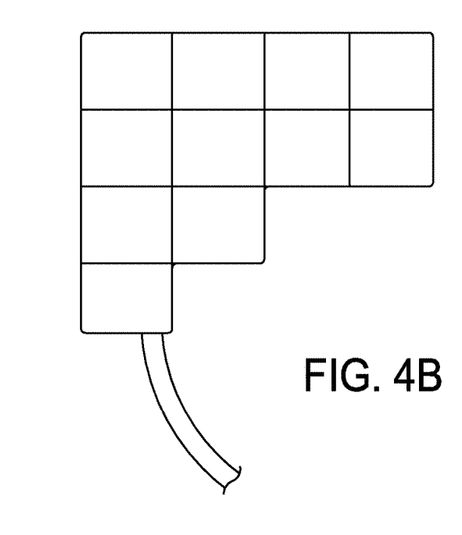
Figure 4C:
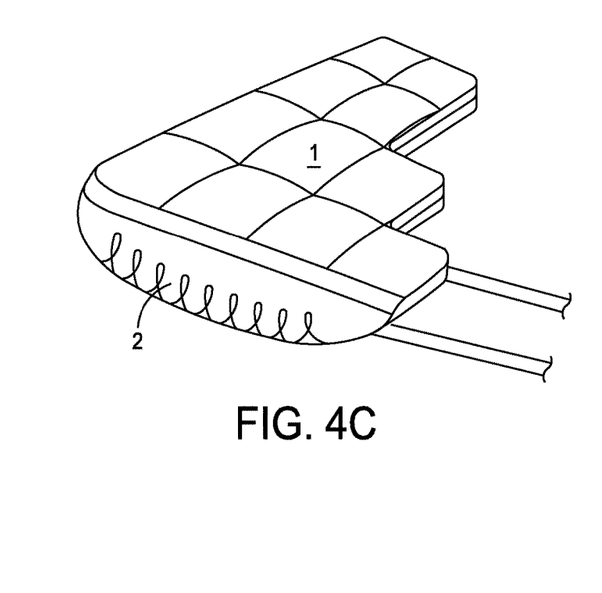

Referring to FIG. 4A, in another embodiment, a device with a stepwise elongation towards a left lower corner or pole (when viewed from above) is shown, with different-sized electrical coils to produce heat. Similarly FIG. 4B shows coupling of individual cells with a surface area shape that elongates moving from right to left, with the largest area being the left lower aspect; these cells may emit ultrasound, microwave, laser, or another energy source. FIG. 4C shows a device similar to the device shown in FIG. 4B when viewed from its right side, with an ablating surface compartment 1, and a separate and underlying component 2 to counteract ablation of compartment 1, actuated or controlled via ports dedicated to each compartment.

Referring back to FIGS. 1A and 1B, in one embodiment, the ablation compartment 1 is connected to a source 12 of nitrous oxide (or another gas/liquid) via port/line 3. The anti-ablation compartment 2 is connected to a source 13 of warm saline solution via port/line 4. In other embodiments, the sources 12, 13 may be electrical energy sources. As mentioned above, the controller 11 is configured to control the operation of the device in accordance to inputs provided by an operator of the device.

The device disclosed herein may embody different configurations. In one embodiment, the first compartment 1 is configured to resorb energy by cryothermy or freezing and the second compartment 2 is configured to emit energy or insulates against croythermy.

In another embodiment, the first compartment 1 is configured to emit energy by radiofrequency, ultrasound, microwave, magnetism or laser and the second compartment 2 is configured to utilize a cooling mechanism.

In certain embodiments, at least one port 3 or 4 communicates with each of the two compartments individually. In another embodiment, at least one port 3 or 4 is used for shuttling gas or liquid.

In one embodiment, with reference to FIGS. 1A and 1B, at least one of the compartments 1 or 2 has integrated temperature sensors, each indicated at 14, to measure or otherwise detect temperature in the compartment. In other embodiments, both compartments 1, 2 have integrated temperature sensors. The sensors 14 are coupled to the controller, e.g., by line 10, to provide information to the controller 11. Based on the feedback from the sensors 14, the controller 11 and/or an operator of the controller can manipulate the flow of material/energy from sources 12, 13 via ports/lines 3, 4, respectively.

This disclosure is not limited in its application to the details of construction and the arrangement of components set forth in the following description or illustrated in the drawings. The principles set forth in this disclosure are capable of being provided in other embodiments and of being practiced or of being carried out in various ways. Also, the phraseology and terminology used herein is for the purpose of description and should not be regarded as limiting. The use of "including," "comprising," "having," "containing," "involving," and variations thereof herein, is meant to encompass the items listed thereafter and equivalents thereof as well as additional items.

Having thus described several aspects of at least one embodiment of this disclosure, it is to be appreciated various alterations, modifications, and improvements will readily occur to those skilled in the art. Such alterations, modifications, and improvements are intended to be part of this disclosure, and are intended to be within the spirit and scope of the disclosure. Accordingly, the foregoing description and drawings are by way of example only.

What is claimed is:

1. A cryoablation device for ablating an exterior surface of an internal organ, the device comprising an ablation body comprising:
  (a) a cryoablation surface defining a portion of a cryoablation compartment;
  (b) an insulation surface defining a portion of an insulation compartment disposed adjacent to the cryoablation compartment;
  (c) a collapsed configuration wherein the ablation body comprises a collapsed size and shape such that the ablation body can be deployed via a minimally invasive procedure;
  (d) an expanded deployment configuration wherein
    (i) the cryoablation surface is a substantially flat and quadrilateral shape and is sized and shaped in the expanded deployment configuration to contact a large planar area of the exterior surface of the internal organ of a patient; and
    (ii) the insulation compartment comprises an inflated configuration wherein the insulation compartment contains an increased amount of an insulation fluid,
  wherein each of the cryoablation surface and the insulation surface has a surface area of at least six $cm^2$ in the expanded deployment configuration;
  (e) an ablation fluid delivery line in fluidic communication with the cryoablation compartment and coupled to a first side of the ablation body; and
  (f) an ablation fluid removal line in fluidic communication with the cryoablation compartment and coupled to the first side of the ablation body, wherein the ablation fluid delivery line is constructed and arranged to deliver an ablation fluid and the ablation fluid removal line is constructed and arranged to remove the ablation fluid such that the ablation fluid is continuously shuttled through the cryoablation compartment, wherein the insulation surface is disposed on an opposite side of the ablation body in relation to the cryoablation surface, and wherein the insulation compartment is configured to insulate surrounding tissues from the cryoablation compartment.

2. The device of claim 1, wherein the cryoablation compartment resorbs energy by cryothermy or freezing.

3. The device of claim 2, wherein the insulation compartment emits energy or insulates against cryothermy.

4. The device of claim 1, wherein the device is collapsible into the collapsed configuration and expandable into the expanded deployment configuration by a roll-up mechanism.

5. The device of claim 1, wherein at least one of the cryoablation compartment and the insulation compartment has integrated temperature sensors.

6. A cryoablation method comprising:
positioning an ablation device adjacent to an exterior surface of an internal organ of a patient, the ablation device comprising an ablation body comprising:
(a) a cryoablation surface defining a portion of a cryoablation compartment; and
(b) an insulation surface defining a portion of an insulation compartment disposed adjacent to the cryoablation compartment;
deploying the ablation body from an uninflated configuration to an inflated configuration, wherein:
the uninflated configuration comprises both the ablation body and the insulation compartment having a collapsed size and shape, and
the inflated configuration comprises the cryoablation surface having a substantially flat and quadrilateral shape and the insulation compartment containing an increased amount of an insulation fluid, wherein each of the cryoablation surface and the insulation surface has a surface area of at least six cm$^2$ in the inflated configuration;
contacting the inflated configuration of the cryoablation surface to a substantial portion of the exterior surface of the internal organ of the patient;
ablating the exterior surface of the target organ by causing the cryoablation surface to resorb energy by delivering an ablation fluid to the cryoablation compartment via an ablation fluid delivery line coupled to a first side of the ablation body and removing the ablation fluid via an ablation fluid removal line coupled to the first side of the ablation body such that the ablation fluid is continuously shuttled through the cryoablation compartment; and
protecting structures disposed adjacent to the insulation surface by insulating the structures from the energy of the cryoablation surface.

7. The method of claim 6, wherein the cryoablation compartment resorbs energy by cryothermy or freezing and the insulation compartment emits energy or insulates against cryothermy.

8. The device of claim 1, wherein the cryoablation surface is sized in the expanded configuration to contact a substantial portion of the posterior wall of the left atrium.

9. The device of claim 1, wherein the cryoablation surface is substantially flat in the expanded deployment configuration.

10. The device of claim 1, wherein the expanded configuration comprises the insulation surface being substantially convex.

11. A cryoablation device for ablating an exterior surface of an internal organ, the device comprising an ablation body comprising:
(a) a cryoablation compartment comprising a cryoablation surface;
(b) an insulation compartment disposed adjacent to the cryoablation compartment, the insulation compartment comprising an insulation surface disposed on an opposite side of the ablation body in relation to the cryoablation surface;
(c) an uninflated configuration wherein the ablation body comprises a collapsed size and shape such that the ablation body can be delivered via a minimally invasive procedure;
(d) an inflated configuration wherein:
the cryoablation compartment and the cryoablation surface comprise a relatively flat and quadrilateral shape, whereby the cryoablation surface is constructed and shaped to contact and conform to a substantial portion of the exterior surface of the internal organ of a patient, and
the insulation compartment comprises an increased amount of an insulation fluid disposed in the insulation compartment,
wherein each of the cryoablation surface and the insulation surface has a surface area of at least six cm$^2$ in the inflated configuration;
(e) an ablation fluid delivery line in fluidic communication with the cryoablation compartment and coupled to a first side of the ablation body; and
(f) an ablation fluid removal line in fluidic communication with the cryoablation compartment and coupled to the first side of the ablation body,
wherein the ablation fluid delivery line is constructed and arranged to deliver an ablation fluid and the ablation fluid removal line is constructed and arranged to remove the ablation fluid such that the ablation fluid is continuously shuttled through the cryoablation compartment,
wherein the insulation compartment is configured to insulate surrounding tissues from the cryoablation compartment.

12. The device of claim 11, wherein the cryoablation surface is substantially flat in the expanded deployment configuration.

13. The device of claim 11, wherein the inflated configuration comprises the insulation surface being substantially convex.

14. The method of claim 6, wherein the deploying the ablation body from the uninflated configuration to an inflated configuration comprises deploying the ablation body with a roll-up mechanism.

15. The method of claim 6, further comprising detecting a temperature via temperature sensors integrated into at least one of the cryoablation compartment and the insulation compartment.

16. The method of claim 6, wherein the exterior surface of the internal organ is the posterior wall of the left atrium.

17. The method of claim 6, wherein the inflated configuration comprises the insulation surface being substantially convex.

18. The device of claim 11, wherein the cryoablation compartment is configured to resorb energy by cryothermy or freezing.

19. The device of claim 11, wherein at least one of the cryoablation compartment and the insulation compartment has integrated temperature sensors.

* * * * *